(12) United States Patent
Acharya

(10) Patent No.: US 12,053,404 B2
(45) Date of Patent: Aug. 6, 2024

(54) SPLITTABLE DELIVERY SHEATH

(71) Applicant: Madan M. Acharya, Des Moines, IA (US)

(72) Inventor: Madan M. Acharya, Des Moines, IA (US)

(*) Notice: Subject to any disclaimer, the term of this patent is extended or adjusted under 35 U.S.C. 154(b) by 0 days.

(21) Appl. No.: 18/231,910

(22) Filed: Aug. 9, 2023

(65) Prior Publication Data
US 2024/0091038 A1  Mar. 21, 2024

Related U.S. Application Data

(60) Provisional application No. 63/408,468, filed on Sep. 20, 2022.

(51) Int. Cl.
*A61F 2/97* (2013.01)
*A61M 25/09* (2006.01)

(52) U.S. Cl.
CPC ............... *A61F 2/97* (2013.01); *A61M 25/09* (2013.01); *A61M 2025/09058* (2013.01); *A61M 2210/125* (2013.01)

(58) Field of Classification Search
CPC ............ A61F 2/97; A61M 25/09; A61M 2025/09058; A61B 17/3415; A61B 17/3417; A61B 17/3421
See application file for complete search history.

(56) References Cited

U.S. PATENT DOCUMENTS

| | | | |
|---|---|---|---|
| 5,755,769 A * | 5/1998 | Richard | A61F 2/90 623/1.2 |
| 6,315,792 B1 | 11/2001 | Armstrong | |
| 6,671,560 B2 | 12/2003 | Westlund et al. | |
| 6,733,500 B2 | 5/2004 | Kelley et al. | |
| 6,758,854 B1 | 7/2004 | Butler et al. | |
| 6,939,327 B2 | 9/2005 | Hall | |
| 7,092,765 B2 | 8/2006 | Geske et al. | |
| 7,637,902 B2 | 12/2009 | Eversull | |
| 7,840,261 B2 | 11/2010 | Rosenman et al. | |
| 8,012,127 B2 | 9/2011 | Lieberman et al. | |
| 8,126,570 B2 | 2/2012 | Manning et al. | |
| 8,938,310 B2 | 1/2015 | Spotnitz et al. | |
| 9,302,078 B2 | 4/2016 | Lieberman et al. | |

(Continued)

FOREIGN PATENT DOCUMENTS

WO   20200183438 A1   9/2020

*Primary Examiner* — Thomas McEvoy
(74) *Attorney, Agent, or Firm* — Bold IP PLLC; Binita Singh

(57) ABSTRACT

A delivery sheath is provided that that can be used to deliver a therapeutic device to the heart without dislodging the device when the delivery sheath is removed. The delivery sheath comprises a tubular body having a proximal end, a distal end, and a lumen. The therapeutic device is delivered through the lumen. A slit is provided along the length of the tubular body creating two opposing edges along the length of the tubular body. A guide wire engages along an entire length of the slit and closing the two opposing edges to form the lumen. The slit is opened from the distal end of the tubular body toward the proximal end of the tubular body by pulling on the guide wire at the proximal end, whereby the lumen expands and separates from the therapeutic device facilitating the extraction of the delivery sheath without disruption to the implanted device.

15 Claims, 9 Drawing Sheets

(56) References Cited

U.S. PATENT DOCUMENTS

| | | |
|---|---|---|
| 9,937,319 B1 | 4/2018 | Leeflang et al. |
| 10,485,435 B2 | 11/2019 | Griswold et al. |
| 10,492,938 B2 | 12/2019 | Lam |
| 10,569,063 B2 | 2/2020 | Cully et al. |
| 2008/0048011 A1 | 2/2008 | Weller |
| 2011/0082342 A1* | 4/2011 | Whitman ........... A61B 17/3439 |
| | | 600/206 |
| 2016/0001042 A1 | 1/2016 | Worley et al. |
| 2019/0282786 A1 | 9/2019 | Raines |
| 2019/0307988 A1 | 10/2019 | Spear et al. |
| 2020/0276417 A1 | 9/2020 | Rentschler et al. |

\* cited by examiner

SPLITTABLE DELIVERY SHEATH

REFERENCE TO RELATED APPLICATIONS

The application is a non-provisional application which claims priority to U.S. Provisional Patent Application No. 63/408,468 filed on Sep. 20, 2022, which is incorporated by reference in its entirety.

FIELD OF THE DISCLOSURE

The present invention relates to sheaths which are utilized in cardiac, vascular, and interventional radiology procedures. More particularly, the present invention relates to a splitable sheath for lead delivery.

BACKGROUND

The myocardium's venous drainage confluences into a large vessel called the coronary sinus, which runs in the posterior aspect of the coronary groove. The coronary sinus may be involved in a number of different procedures and may act as a conduit for access to various locations within the heart.

Traditionally, cardiac electrophysiologists have placed a pacing lead in a branch of the coronary sinus to help improve heart failure symptoms in select individuals. Delivery of a coronary sinus or left ventricular lead from an intra-vascular approach is often challenging and at times impossible to achieve given present techniques of implantation. Of the many challenges that an implanting physician faces, lead stability during final stages of coronary sinus lead placement is commonplace. The final stages of the left ventricular lead placement involve removal of the delivery sheath from the body while leaving the lead in the desired branch of the coronary sinus. The current approach to delivery sheath removal involves splitting the delivery sheath from the proximal end outside the body and gradually pulling the sheath out of the heart and out of the body. The sheath is split as it is being pulled out of the circulatory system using a splitting tool provided by the industry while leaving the lead in place. The challenge often is to ensure that the lead is minimally disturbed and maintained at the delivery site while the sheath is extracted. Implementation difficulty occurs when the sheath dislodges the lead as it is being split and removed from the body. Therefore, in such a situation, the procedure may need to be restarted to reimplant the lead, which requires reengagement of the entire procedure by the physicians and staff. Further, this could result in adverse outcomes for the patient such as longer procedure times, exposure to prolonged duration of anesthesia, and a higher risk of procedure related complications such as infections.

A modification in the coronary sinus lead delivery system is likely to benefit the implanting physician and the patient undergoing a procedure requiring such a system. Accordingly, there exists a need for an improved means of splitting and removing a lead delivery sheath from the body that does not dislodge or disrupt the implanted lead.

SUMMARY

One or more embodiments are provided below that address the foregoing problems, among others, by providing for a coronary sinus lead delivery sheath. In one implementation, the delivery sheath defines a lumen through which a lead is delivered to an implantation site. The delivery sheath is designed to be splitable from a distal end whereby the lumen expands and separates from the lead, thus facilitating the extraction of the delivery sheath without disruption to the implanted lead.

In one example embodiment, a delivery sheath is configured to split from a distal end wherein the delivery sheath comprises of a longitudinal split wherein the split extends an entire length of the delivery sheath. The split is adjoined by multiple segments along each edge defined by the split. The multiple segments on a first seam and a second seam are staggered whereby the multiple segments align together to from a lumen. Each of the multiple segments include an opening whereby the openings in each of the multiple segments longitudinally align when the multiple segments are placed together to form the lumen. A release wire is included, which traverses through the openings in the multiple segments disposed along an entire length of the split such that the delivery sheath is coupled together at the longitudinal split. The split is formed as the guide wire is pulled out and the split forms from a distal end of the delivery sheath (the end inserted into the body) and thereby opening the delivery sheath from the distal end to the proximal end.

Other aspects and advantages of the invention will be apparent from the following description and the appended claims taken in conjunction with the accompanying drawings.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

Figure 1:
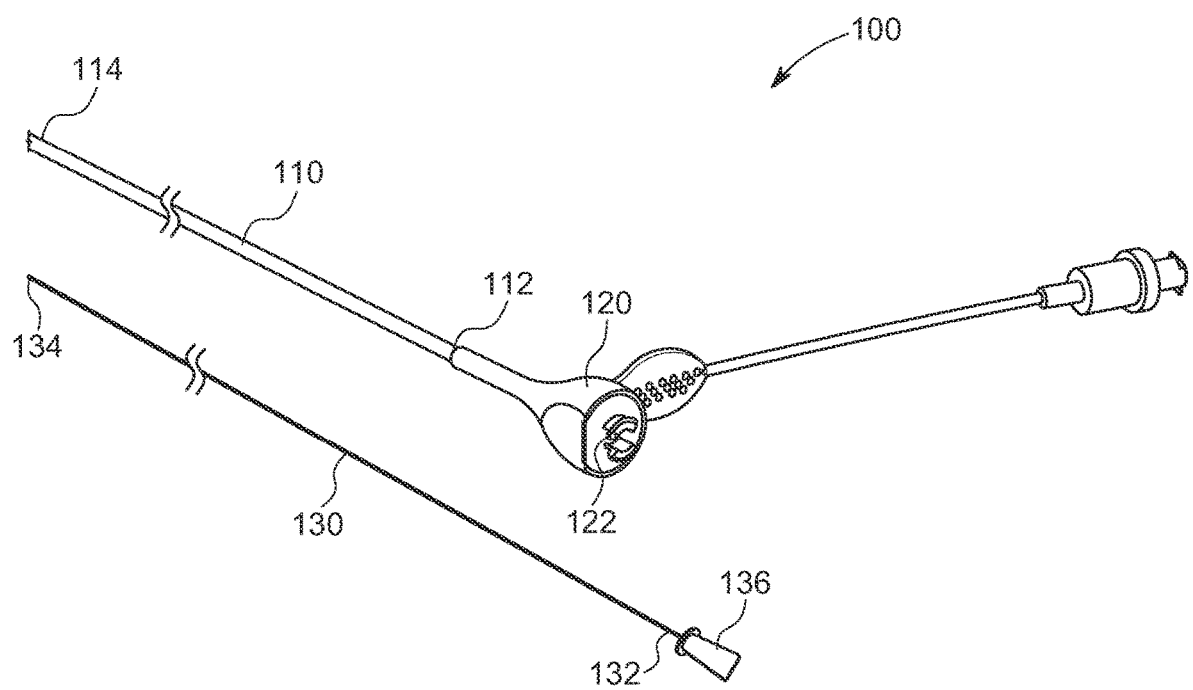
FIG. 1 is a pictorial illustration of a delivery sheath system.

In the Summary above and in this Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, among others, are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm and upper limit is 100 mm.

Certain terminology and derivations thereof may be used in the following description for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "coupled to" as used herein may mean a direct or indirect connection via one or more components.

The present disclosure is generally drawn to various embodiments for a splittable delivery sheath that can be used to deliver a therapeutic device to the heart. An example use for the delivery sheath system may be in coronary sinus lead placement procedures. In accordance with one or more embodiments, the splittable delivery sheath may be provided that allows controlled splitting starting from a distal end toward a proximal end of the delivery sheath, whereby splitting distally is less likely to dislodge an implanted lead as much of the tortuosity in maneuverability of the sheath as it is retracted lies at the Os of the coronary sinus.

The terms "distal" and "distally" refers to a relative location that is farther from a location in the body at which the delivery sheath was introduced. Further, the terms "proximal" and "proximally" refer to a relative location that is closer to the location in the body at which the delivery sheath was introduced.

Turning to the figures, FIGS. 1 to 5 illustrate an example embodiment of a splittable delivery sheath system. FIG. 1 is an illustration depicting a perspective view of an example embodiment of the splittable delivery sheath system 100. It is to be understood that the images are not drawn to scale and represent the elements of the present invention. It is noted that the splittable delivery sheath system 100 may be interchangeably used with the words "delivery sheath system" or "sheath system" for purposes of brevity. In one or more non-limiting embodiments, the delivery sheath system 100 is suited or adapted for use as a conduit for delivery of a device, such as a pace lead.

The delivery sheath system 100 is shown to include a delivery sheath 110 and a guide wire 130. In FIG. 1 the guide wire 130 is shown alongside the delivery sheath 110, however, the guide wire 130 is operatively coupled to the sheath 110 to provide for a delivery sheath 100 with a lumen for navigating and delivering an implantable device (e.g., pace lead) or other therapeutic devices. The guide wire 130 is removed from the delivery sheath 110 to split the delivery sheath 110. As the guide wire 130 is removed, the delivery sheath 110 starts to split from a distal end 114 toward a proximal end 112. The delivery system 100 can include various separation means for distally removing the delivery sheath 110 from a therapeutic device when the therapeutic device is delivered and implanted to a tissue. The guide wire 130 is one example of the various embodiments of the present disclosure where the delivery sheath 110 is split distally for extraction.

In one or more non-limiting embodiments, the delivery sheath 110 is like most other sheaths described in the arts, where the proximal end 112 of the delivery sheath 110 is coupled to a handle 120 and the distal end 114 is inserted into a vein. The delivery sheath 110 includes a lumen (see, FIG. 2, lumen 102) that extends through an entire length of the delivery sheath 110 extending from the proximal end 112 to the distal end 114. The lumen 102 extends into the handle 120 with an opening 122 that allows a pace lead or other appropriate device, such as a lead delivery guide, to be inserted into the delivery sheath 110 and navigated through the lumen 102 to an opening at the distal end 114.

FIG. 1 also illustrates that the guide wire 130 is in a form of a thin rod which may be flexible or inflexible. The guide wire 130 is an elongated thin rod which has a first end 132 and a second end 134. The first end 132 includes a grip 136 which is designed to allow a user to hold and pull the guide wire 130. The guide wire 130 is designed to fit through the opening 122 in the handle 120 coupled to the delivery sheath 110. The guide wire 130 extends through the delivery sheath 110 and has a length that extends an entire length of the delivery sheath 110. In particular, the grip 136 remains outside of the handle 120 at the opening 122 and the second end 134 of the guide wire 130 extends up to the opening at the distal end 114 of the delivery sheath 110. The second end 134 of the guide wire 130 does not extend past the opening of the distal end 114. The guide wire 130 remains flush or relatively close to the opening in the distal end 114 of the delivery sheath 110 such that the guide wire 130 does not cause any injury as the delivery sheath 110 coupled to the guide wire 130 is navigated through a bodily cavity.

Figure 2:
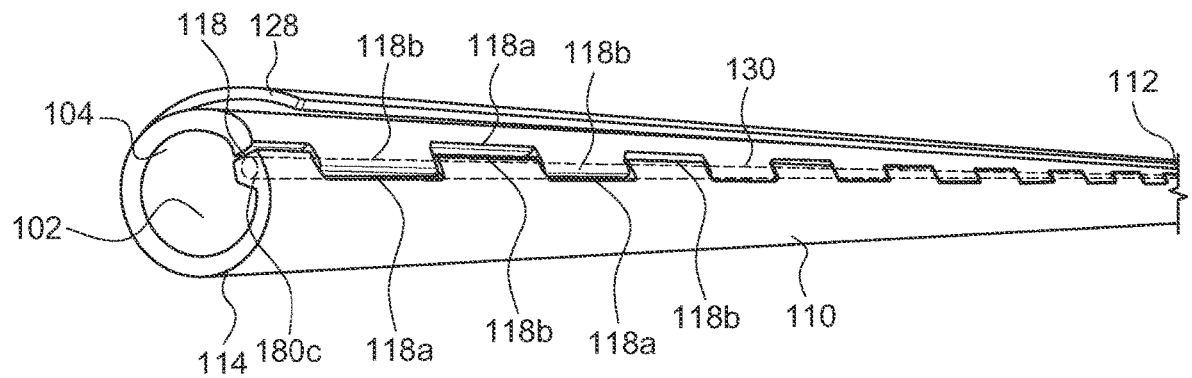
FIG. 2 is a pictorial illustration of a side perspective view of a delivery sheath comprising part of the delivery sheath system in accordance with an illustrative embodiment.
Figure 3:
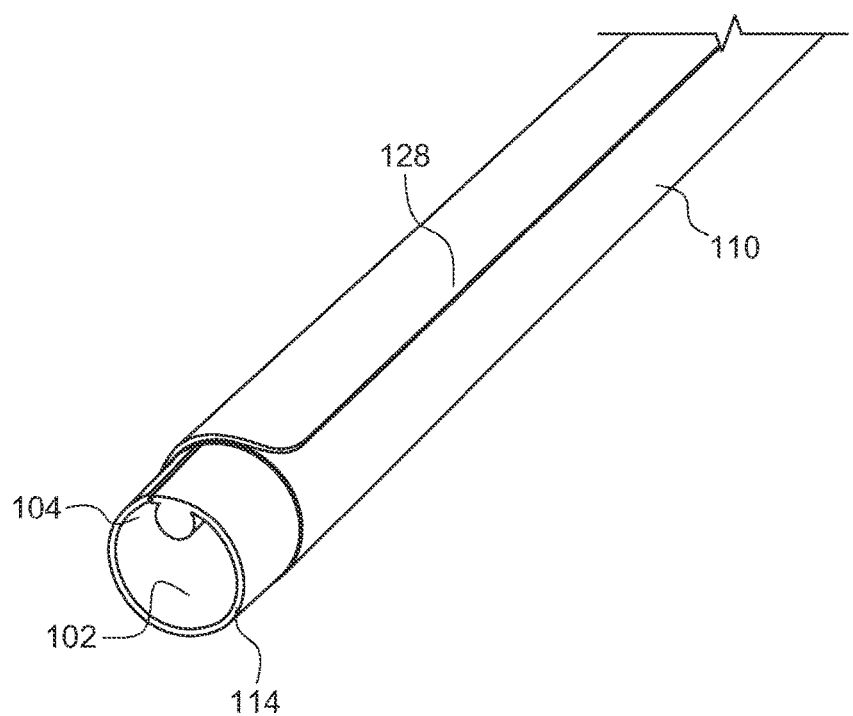
FIG. 3 is a pictorial illustration of a top perspective view of the delivery sheath comprising part of the delivery sheath system in accordance with an illustrative embodiment.
Figure 4:
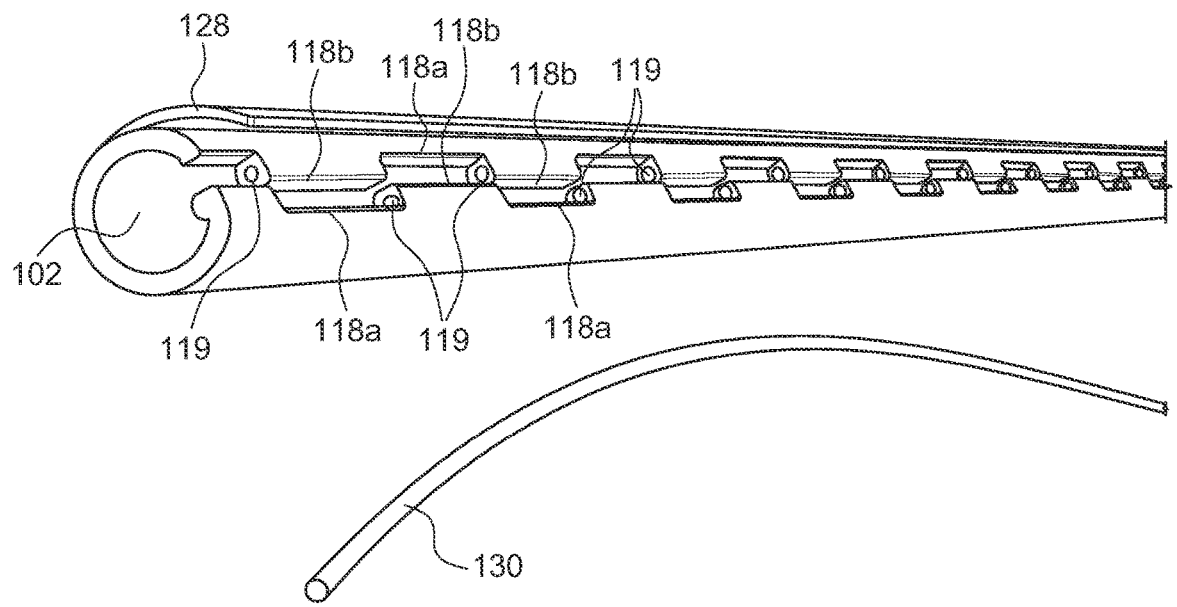
FIG. 4 is a pictorial illustration of a side perspective view of the delivery shaft and a guide wire in accordance with an illustrative embodiment.

FIGS. 2 to 5 further depict elements of the delivery sheath system 100. FIGS. 2 to 4 depict a close-up illustration of the delivery sheath 110 which includes a slit 118, configured to structurally separate the delivery sheath 110 along the slit 118. The slit 118 has a segmented configuration which may extend through the entire length of the delivery sheath 110 from the distal end 114 to the proximal end 112 wherein the slit 118, when adjoined, is along a relatively straight line. The slit 118 is formed by a series of segmented sections, which are defined by a plurality of indentations 118a and a plurality of tabs 118b along each edge of the slit 118. The plurality of indentations 118a and the plurality of tabs 118b alternate along the entire length of the slit 118 along each edge defined by the slit 118. As seen in FIG. 2, the plurality of indentations 118a and the plurality of tabs 118b are configured and sized such that a single tab 118b along one edge of the slit 118 fits within a single indentation 118a along the alternate edge of the slit 118. Operably, each of the plurality of tabs 118b fit within each of their corresponding plurality of indentations 118a directly opposite each tab 118b to form the lumen 102 in the delivery sheath. In other words, the plurality of indentations 118a and plurality of tabs 118b align and engage with each other to form the lumen 102. The guide wire 130 assists in closing the slit 118 to form the lumen 102, which will be discussed below.

Figure 5:
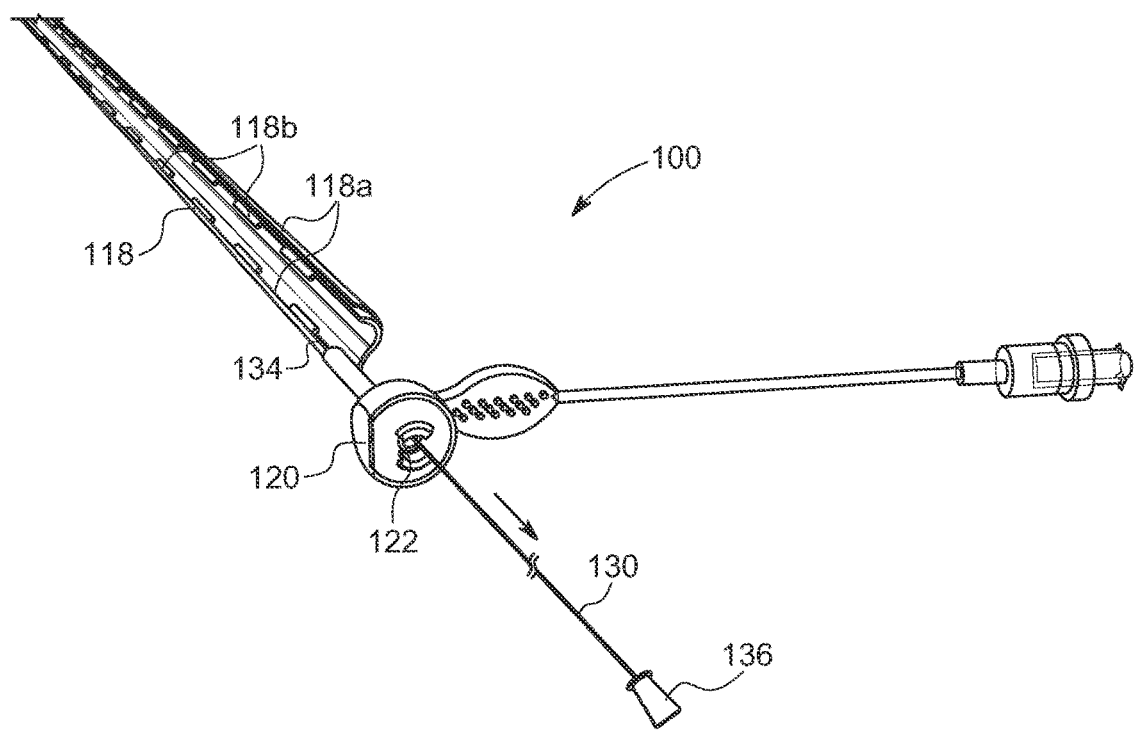
FIG. 5 is a pictorial illustration of a delivery sheath system depicting an open delivery sheath in accordance with an illustrative embodiment.

Referring to FIG. 4, the delivery sheath 110 is shown with the guide wire 130 removed to offer a more detailed illustration of the plurality of indentations 118a and the plurality of tabs 118b. As best seen in FIG. 4, each of the plurality of tabs 118b includes a hole 119 that traverses an entire length of each of the plurality of tabs 118b. The holes 119 are configured to allow the guide wire 130 to fit through. In the various embodiments described above, the plurality of tabs 118b fit within the plurality of indentations 118a, such that the plurality of tabs 118b abut with each of the holes 119 aligned for the guide wire 130 to extend through to form the lumen 102 in the delivery shaft 110. As mentioned above, the guide wire 130 is placed through the handle 120 extending through the holes 119 traversing the entire length of the delivery shaft 110 with the grip 136 of the guide wire remaining exterior to the handle 120. A distal most tab 118b on the delivery sheath 110 (or the last tab 118b at the distal end 114 of the delivery sheath 110) may include the hole 119 that is closed at a distal end of the hole 119. This ensures that the guide wire 130 does not extend past the distal end 114 of the delivery sheath 110. It is to be understood, that alternatively, the hole 119 is not closed and the guide wire 130 has a length that does not extend past the distal end 114 of the delivery sheath 110, as discussed earlier. As shown in FIG. 5, the guide wire 130 may be extracted from the delivery shaft 110 by pulling on the grip 136 to allow the split 118 in the delivery sheath 110 to sequentially open from the distal end 114 as the guide wire 130 is removed from the plurality of tabs 118b and plurality of indentations 118a.

Further, FIGS. 2 to 4 also depict a flap 128 comprising the delivery sheath system 100. The flap 128 is attached along the entire length of the delivery shaft 110 from the proximal end 112 to the distal end 114. The flap 128 may be integrally attached to a top surface of the delivery shaft 110 relatively proximal to the slit 118, such that the flap overhangs over the slit 118. The flap 128 may be uniformly attached along the entire length of the delivery shaft 110 and configured to cover the entire length of the slit 118. The flap 128 provides a smooth profile to the slit 118 especially when the guide wire 130 is removed exposing any edges that may be associated with the plurality of indentations and tabs 118a, 118b. Thus, the smooth structural profile of the slit 118 provides a cover to reduce any chances of injury from any exposed edges on the delivery shaft 110.

Figure 6A:
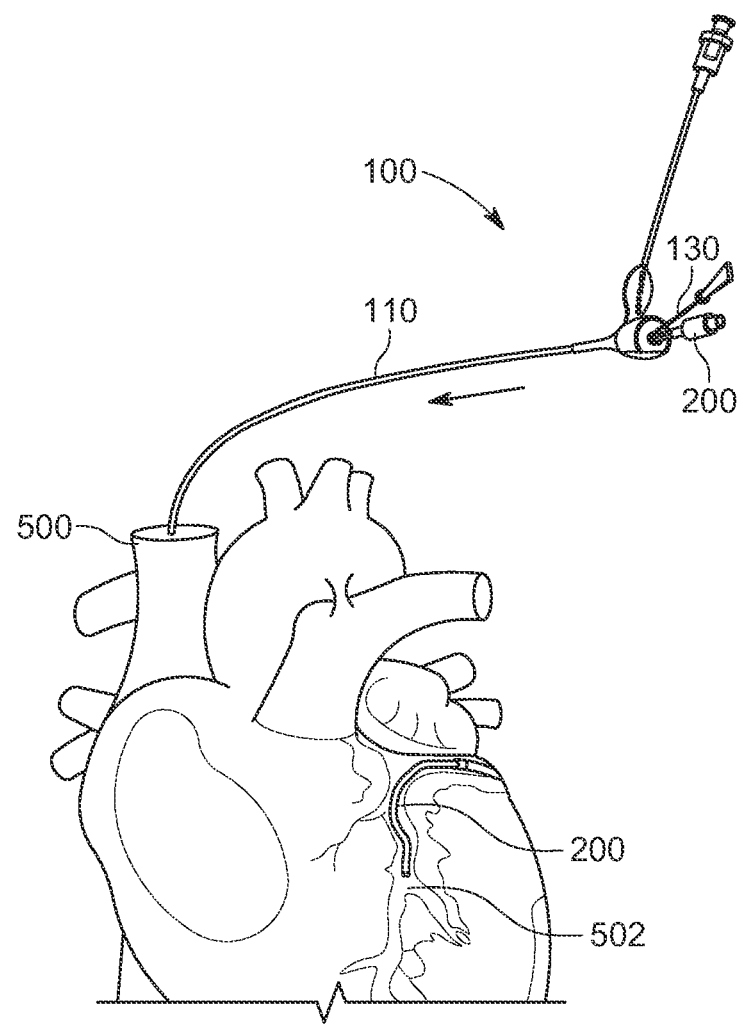
FIG. 6A is a pictorial illustration of a step in the placement of a pace lead in the heart in accordance with an illustrative embodiment.
Figure 6B:
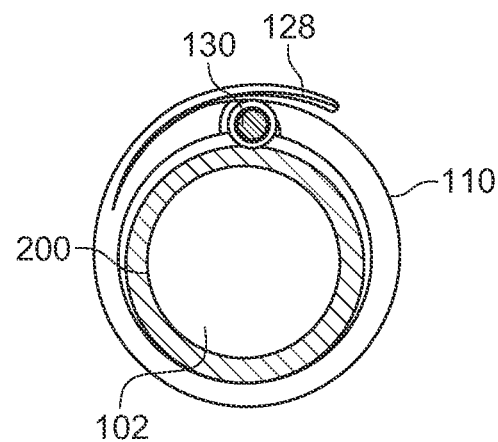
FIG. 6B is a cross sectional view of the delivery shaft and a guide insert depicted in FIG. 6A.

FIGS. 6A to 9B illustrate an example use of the delivery sheath system 100 in use during a procedure. FIGS. 6A and 6B illustrate the start of the procedure requiring a placement of a pace lead through the coronary sinus. In FIG. 6A, the delivery sheath system 100 with an inner dilator 200 are inserted into the coronary sinus 500 to enter a branch vessel 502. FIG. 6B illustrates a cross sectional view of the delivery sheath 110 and the inner dilator 200. In FIG. 6B, the inner dilator 200 is shown inserted into the lumen 102 of the delivery sheath 110. As clearly seen, the guide wire 130 remains within the delivery sheath 110 and the flap 128 is covering the slit (not seen in the illustration). Once the delivery sheath system 100 is inserted into the desired branch vessel, the inner dilator 200 is extracted from within the delivery sheath system 100.

Figure 7A:
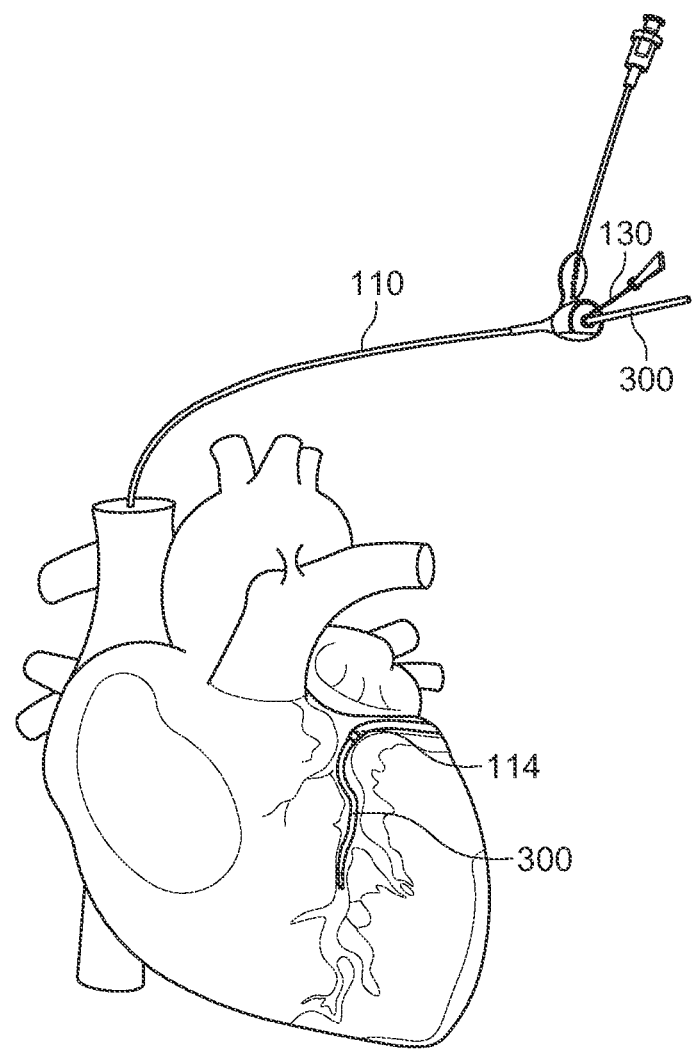
FIG. 7A is a pictorial illustration of a step in the placement of the pace lead in the heart in accordance with an illustrative embodiment.
Figure 7B:
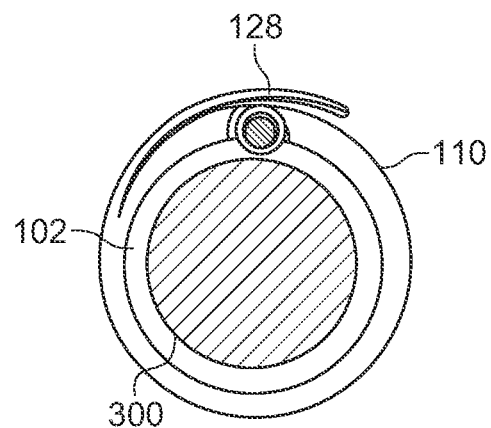
FIG. 7B is a cross sectional view of the delivery shaft and a pace lead depicted in FIG. 7A.

FIGS. 7A and 7B illustrate the next step in the example procedure, where a lead 300 is inserted into the delivery sheath system 100 from the handle 120 and through the delivery sheath 110 into the branch vessel where the distal end 114 of the delivery sheath 110 is located. The lead 300 is inserted through the delivery sheath 110 till it enters the vessel through the distal end 114 of the delivery sheath 110. The lead is attached to the tissue at the desired location. FIG. 7b illustrates a cross sectional view of the lead 300 inserted within the delivery sheath 110. As seen, the lumen 102 of the delivery sheath is still intact with the guide wire 130 remaining within the delivery sheath 110.

Figure 8A:
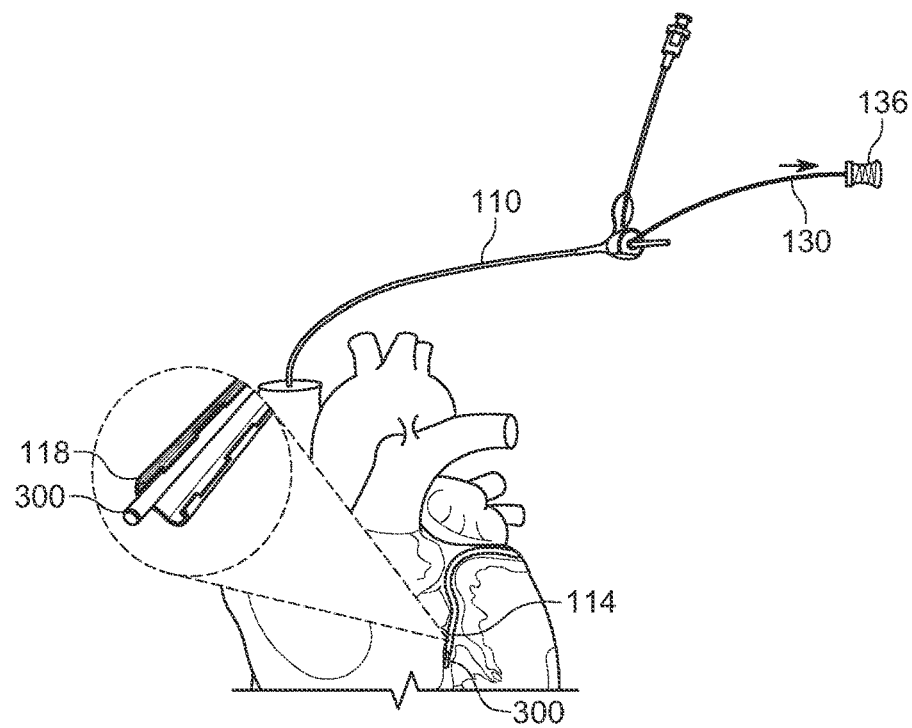
FIG. 8A is a pictorial illustration of the distally splitting of the delivery shaft after placement of a pace lead in the heart in accordance with an illustrative embodiment.
Figure 8B:
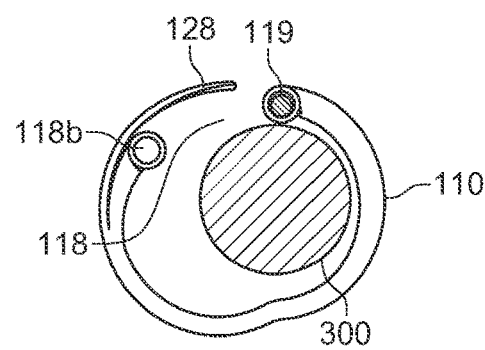
FIG. 8B is a cross sectional view of the delivery shaft and the pace lead with the delivery shaft being split distally depicted in FIG. 8A.
Figure 8C:
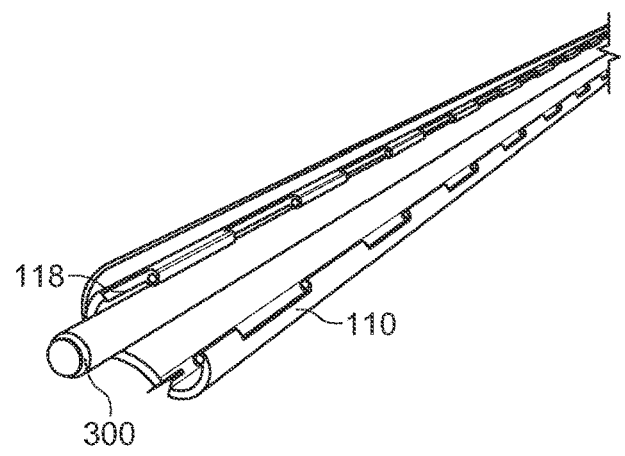
FIG. 8C is a pictorial illustration depicting the delivery shaft and pace lead from FIG. 8A with the delivery shaft split open.

FIGS. 8A to 8C illustrate extraction of the delivery sheath after the pace lead has been implanted at the desired location. The delivery sheath 110 is extracted by commencing the splitting of the sheath 110 distally and moving proximally. Thus, the slit 118 at the distal end of the delivery sheath 110 is opened first by pulling out the guide wire 130. As the guide wire 130 is pulled out by using the grip 136, the guide wire is removed from the holes 119 in the plurality of tabs defining the slit 118. As the guide wire 130 is pulled out, the lumen 102 of the delivery sheath 110 opens and moves away from the pace lead. Thus, the delivery sheath 110 is easier to remove without dislodging or disrupting the pace lead as the delivery sheath 110 contact with the lead is minimal.

Figure 9A:
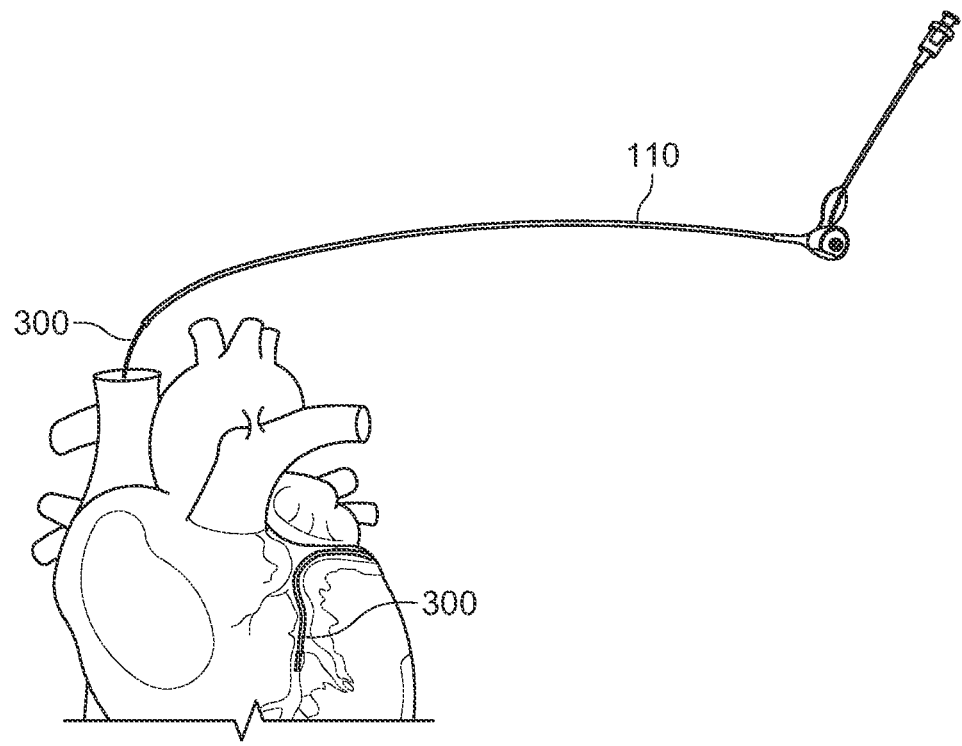
FIG. 9A is a pictorial illustration of a delivery shaft removal step in the placement of a pace lead in the heart in accordance with an illustrative embodiment.
Figure 9B:
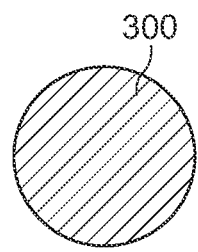
FIG. 9B is a pictorial illustration depicting the lead only after removal of the delivery shaft.

FIGS. 9A and 9B illustrate the full removal of the delivery shaft from within the vessel after the pace lead has been implanted. The cross section in FIG. 9B illustrates that the pace lead 300 is free of the delivery shaft 110.

Figure 10A:
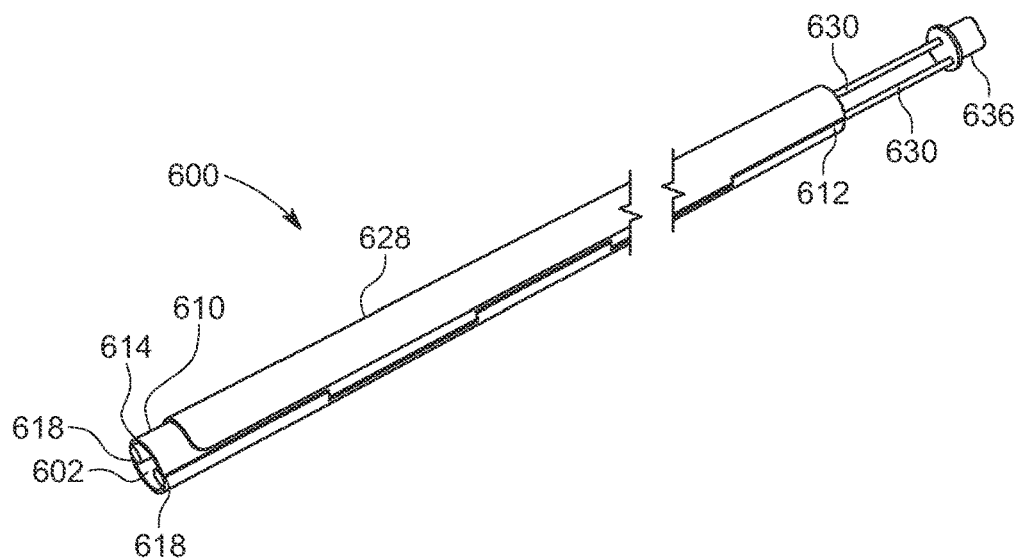
FIG. 10A is a pictorial illustration of an alternate embodiment of a distally splitting delivery shaft system.
Figure 10B:
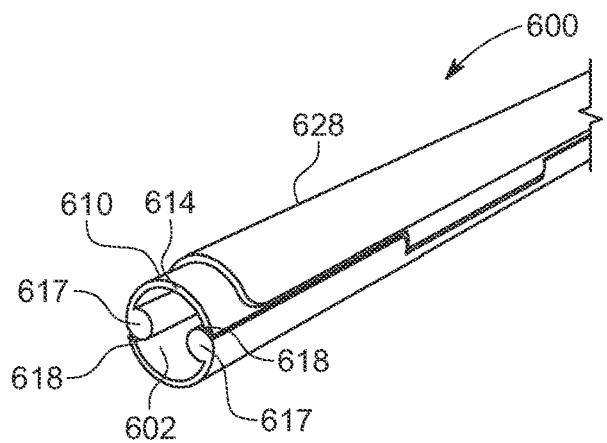
FIG. 10B is a pictorial illustration of a closer view of the alternate embodiment.
Figure 10C:
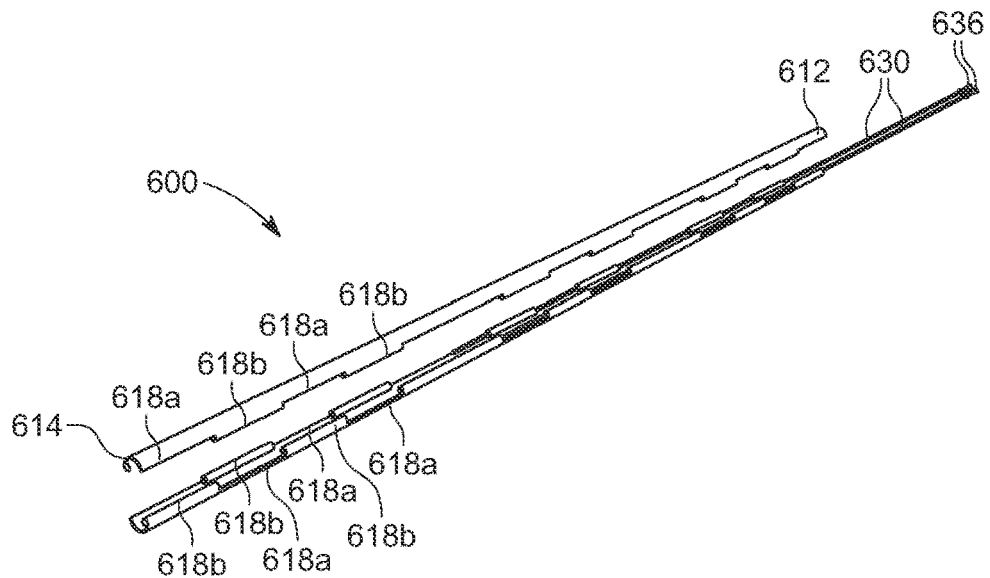
FIG. 10C is a pictorial illustration depicting the alternate embodiment of the distally splitting delivery shaft system in a split position.

Removal of the delivery shaft by splitting the delivery shaft from the distal end can be achieved in other ways. The above is an example of one embodiment that may achieve distally splitting the delivery shaft. An alternate embodiment is illustrated in FIGS. 10A to 10C, which shows a delivery shaft 600 includes a delivery sheath 610 that may include two slits 618 wherein the slits are diagonally opposite each other. The delivery shaft 600 is shown without a coupled handle (for e.g., see FIG. 1, handle 120). Each of the slits 618 may include a plurality of indentations 618a and a plurality of tabs 618b. The plurality of tabs 618b each include holes (see delivery shaft 100 for holes 119) for a guide wire 630. Thus, the alternate embodiment would comprise of two guide wires 630 with each having a grip 636, wherein each slit 618 will accommodate one guide wire 636 and operate as described above. The plurality of tabs 618a at a distal end 614 of the delivery sheath 610 are closed 617 such that the guide wire 630 does not extend past the distal end 614 to prevent any injury or abrasions when placed inside a cavity during a procedure. In this embodiment, the delivery shaft 600 will split a lumen 602 into two sections once the guide wires 630 are removed from the slits 618 and thus separating the delivery shaft from a pace lead or other therapeutic device extended through the delivery shaft lumen and implanted at a site.

Figure 11A:
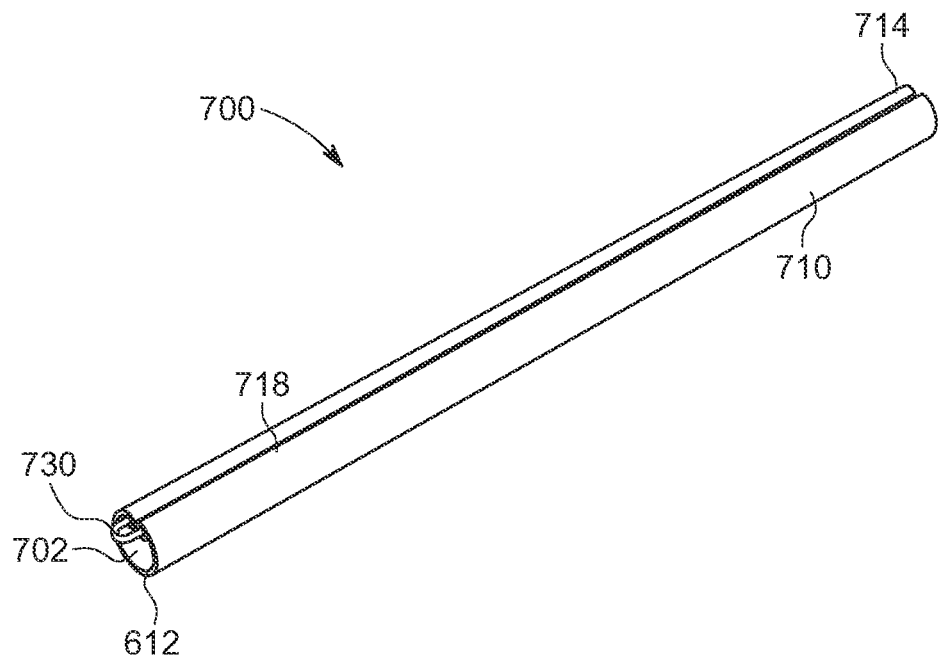
FIG. 11A is a pictorial illustration of a perspective view of an alternate embodiment of a distally splitting delivery shaft system.
Figure 11B:
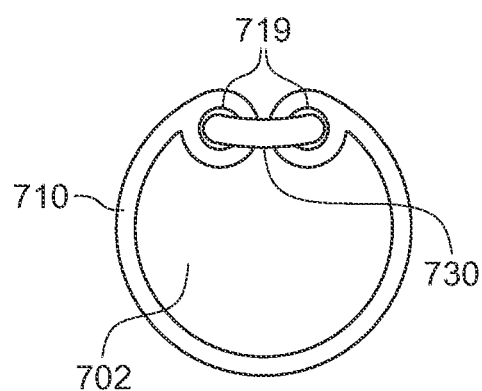
FIG. 11B is a pictorial illustration of a front view of the alternate embodiment of FIG. 10A.

Referring to FIGS. 11A and 11B, an alternate embodiment of a delivery shaft 700 is also shown without a coupled handle (for e.g., see FIG. 1, handle 120). The delivery shaft 700 is shown with a delivery shaft 710 and a guide wire 730 wherein the delivery shaft is capable of being split and opened from a distal end 714. In this embodiment, the delivery shaft 710 includes a slit 718, wherein the slit 718 is also configured along an entire length of the delivery shaft 710 and the slit 718 allows a lumen 702 of the delivery shaft to be opened along the entire length of the delivery shaft 710. The slit 718 is defined by two adjacent holes 719 that are configured along an entire length of the slit 718 on either side of the slit 718. The guide wire 730 has two parallel rods that are connected at a proximal end 712 of the delivery shaft 710. The guide wire 730 is placed within the holes 719 and traverse the entire length of the delivery shaft 710 to form and hold the lumen 702. FIG. 11B illustrates the front view of the delivery shaft 710 and shows the lumen 710. To open the slit 718 and in turn open the lumen 702 of the delivery shaft 710 from the distal end 714, the guide wire 730 is pulled out from within the holes which starts to open the delivery shaft 710 from the distal end 714.

Accordingly, the present description provides for various embodiments for a splittable delivery shaft that is capable of being split from the distal end. Many uses and advantages are offered by the splittable delivery shaft as described above in one or more non-limiting embodiments.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A delivery sheath, comprising:
a tubular body having a proximal end, a distal end, and a length forming a lumen defining an inner surface;
a slit provided along the length of the tubular body, wherein the slit extends between the proximal end and the distal end of the tubular body and creates two opposing edges along the length of the tubular body;
a guide wire that engages with the slit extending between the proximal end and the distal end to close the two opposing edges to form the lumen of the tubular body;
a flap integrally attached to an outer surface of the tubular body, wherein the flap is adjacent to the slit such that the flap overhangs over an entirety of the length of the slit providing a cover over the slit; and
wherein the slit is opened from the distal end of the tubular body toward the proximal end of the tubular body by pulling on the guide wire at the proximal end of the tubular body.

2. The delivery sheath of claim 1, wherein the proximal end is coupled to a handle having an opening that extends to the lumen for delivering therapeutics to a tissue.

3. The delivery sheath of claim 2, wherein the guide wire engages with the slit of the tubular body through the opening in the handle.

4. The delivery sheath of claim 2, wherein the guide wire has a length extending an entire length of the tubular body including the handle, wherein a first end of the guide wire remains outside of the handle, and a second end of the guide wire extends up to the distal end of the tubular body without extending past the distal end of the tubular body.

5. The delivery sheath of claim 4, wherein the first end of the guide wire includes a grip providing a hold for a user to pull on the guide wire.

6. The delivery sheath of claim 1, wherein the slit is configured [with] of segmented sections that align with each other along a straight line.

7. The delivery sheath of claim 6, wherein the segmented sections comprise a plurality of tabs and a plurality of indentations alternatively arranged along each edge of the two opposing edges, and wherein the plurality of tabs along the each edge aligns with the plurality of indentations on an opposing edge of the two opposing edges.

8. The delivery sheath of claim 7, wherein each tab of the plurality of tabs includes a hole that traverses through a length of each tab, such that the guide wire traverses through the hole in each of the tabs of the plurality of tabs when the segmented sections are aligned with each other, whereby the guide wire assists in closing the slit to form the lumen.

9. A delivery sheath, comprising:
a tubular body having a proximal end, a distal end, and a length forming a lumen defining an inner surface;

a pair of slits provided along the length of the tubular body, wherein the pair of slits are parallel to each other extending between the proximal end and the distal end of the tubular body, whereby the two slits separate the tubular body into two pieces, a first piece and a second piece, with each piece of the two pieces having two edges along the length of the pair of slits on the tubular body;

a guide wire for each slit of the pair of slits, wherein each guide wire extends between the proximal end and the distal end to adjoin the two pieces of the tubular body to form the lumen;

a pair of flaps integrally attached to an outer surface of the tubular body, wherein each slit of the pair of slits has a flap from the pair of flaps, wherein each flap of the pair of flaps is adjacent to the respective slit such that each of the flaps of the pair of flaps overhangs over an entirety of the length of a respective slit and provides a cover for each of the pair of slits; and wherein the pair of slits are opened from the distal end of the tubular body toward the proximal end of the tubular body by pulling on the guide wire for the each slit of the pair of slits at the proximal end of the tubular body.

10. The delivery sheath of claim 9, wherein the proximal end of the tubular body is coupled to a handle with an opening that extends to the lumen for delivering therapeutics to a tissue.

11. The delivery sheath of claim 10, wherein the guide wire for the each slit of the pair of slits, engages with a respective slit of the pair of slits through the opening in the handle.

12. The delivery sheath of claim 10, wherein each guide wire for each slit of the pair of slits has a length extending an entire length of the tubular body including the handle, wherein a first end of the guide wire remains outside of the handle, and a second end of the guide wire extends up to the distal end of the tubular body without extending past the distal end of the tubular body.

13. The delivery sheath of claim 9, wherein each slit of the pair of slits is configured of segmented sections that align with each other along a straight line.

14. The deliver sheath of claim 13, wherein the segmented sections comprise a plurality of tabs and a plurality of indentations alternatively arranged along each edge of the two edges of the first piece and the second piece, wherein the plurality of tabs along each edge align with the plurality of indentations on an opposing edge forming the lumen.

15. The delivery sheath of claim 14, wherein each tab of the plurality of tabs includes a hole that traverses through a length of the each tab, such that the guide wire for the each slit traverses through the hole in the each tab of the plurality of tabs when the segmented sections are aligned with each other, whereby the guide wire for the each slit of the pair of slits assists in closing the pair of slits to form the lumen.

* * * * *